United States Patent
Laitinen

(10) Patent No.: US 7,662,964 B2
(45) Date of Patent: Feb. 16, 2010

(54) PROCESS FOR PRODUCING [1,4']BIPIPERIDINYL-1'-CARBONYL CHLORIDE OR HYDROCHLORIDE THEREOF

(75) Inventor: Ilpo Laitinen, Espoo (FI)

(73) Assignee: Fermion Oy, Espoo (FI)

( * ) Notice: Subject to any disclaimer, the term of this patent is extended or adjusted under 35 U.S.C. 154(b) by 99 days.

(21) Appl. No.: 11/883,578

(22) PCT Filed: Feb. 6, 2006

(86) PCT No.: PCT/FI2006/000032

§ 371 (c)(1),
(2), (4) Date: Oct. 3, 2007

(87) PCT Pub. No.: WO2006/084940

PCT Pub. Date: Aug. 17, 2006

(65) Prior Publication Data

US 2008/0161571 A1    Jul. 3, 2008

Related U.S. Application Data

(60) Provisional application No. 60/650,535, filed on Feb. 8, 2005.

(51) Int. Cl.
   *C07D 211/00*      (2006.01)
(52) U.S. Cl. ..................................... 546/189
(58) Field of Classification Search ............... 546/189
   See application file for complete search history.

(56) References Cited

U.S. PATENT DOCUMENTS

| 4,473,692 | A | 9/1984 | Miyasaka et al. |
| 4,604,463 | A | 8/1986 | Mlyasaka et al. |
| 4,894,456 | A | 1/1990 | Wall et al. |
| 5,053,512 | A | 10/1991 | Wani et al. |
| 6,121,451 | A | 9/2000 | Henegar et al. |
| 6,444,820 | B1 | 9/2002 | Henegar et al. |
| 6,476,043 | B1 | 11/2002 | Toutain et al. |
| 6,723,729 | B2 | 4/2004 | Henegar |
| 2004/0106830 | A1 | 6/2004 | Ogawa et al. |
| 2008/0103309 | A1 | 5/2008 | Laitinen |
| 2008/0182990 | A1* | 7/2008 | Vishnukant et al. ........... 546/48 |

FOREIGN PATENT DOCUMENTS

| EP | 1 378 505 A1 | 1/2004 |
| WO | WO-96/31513 A1 | 10/1996 |
| WO | WO-02/066416 A1 | 8/2002 |
| WO | WO-03/074527 A1 | 9/2003 |
| WO | WO-03/089413 A1 | 10/2003 |
| WO | WO 2005/117879 A1 | 12/2005 |

OTHER PUBLICATIONS

Sawada et al., "Synthesis and Antitumor Activity of 20(S)-Camtpthecin Derivatives: Carbamate-Linked, Water-Soluble Derivatives of 7-Ethyl-10-Hydroxycamptothecin," Chemical and Pharmaceuticla Bulletin, Pharmaceuticla Society of Japan, vol. 39, No. 6, 1991, pp. 1446-1454, XP000653715, ISSN: 0009-2363.

Henegar et al., "Pratical Asymmetric Synthesis of (S)-4-Ethyl-7,8dihydro-4-hydroxy-1H-pyrano[3,4-f]indolizine-3,6,10(4H)-trione, a Key Intermediate for the Synthesis of Irinotecan and Other Camptothecin Analogs," Journal of Organic Chemistry, American Chemical Society, vol. 62, No. 19, 1997, pp. 6588-6597, ZP002322583, ISSN: 0022-3263.

Shtske et al., "A novel synthesis of the isoxazolo[5,4,3-kl]acriding ring system," J. Heterocyclic Chem., vol. 27, No. 6, 1990, pp. 1617-1621, XP002386600.

Third Party Observations under Article 115 EPC—EP Application No. 06 708 891.4 (EP 1 846 371) (May 16, 2009).

Third Party Observations Pursuant to Article 115 EPC—EP Application No. 06 708 891.4 (EP 1 846 371) (Apr. 17, 2009).

* cited by examiner

*Primary Examiner*—D. Margaret Seaman
*Assistant Examiner*—Niloofar Rahmani
(74) *Attorney, Agent, or Firm*—Birch, Stewart, Kolasch & Birch, LLP.

(57) ABSTRACT

The present invention is related to a process for the preparation of [1,4']bipiperidinyl-1'-carbonyl chloride or its hydrochloride using methylene chloride as a solvent in the reaction of 4-piperidinopiperidine with phosgene and the removing the reaction solvent by using an additional distillation solvent to raise the distillation temperature.

10 Claims, No Drawings

PROCESS FOR PRODUCING [1,4'] BIPIPERIDINYL-1'-CARBONYL CHLORIDE OR HYDROCHLORIDE THEREOF

This application is the National Phase of PCT/FI2006/000032 filed on Feb. 6, 2006, which claims priority under 35 U.S.C. §119(e) on U.S. Provisional Application No(s). 60/650,535 filed on Feb. 8, 2005, the entire contents of which are hereby incorporated by reference.

FIELD OF THE INVENTION

The invention is related to the process for the preparation of [1,4']bipiperidinyl-1'-carbonyl chloride or its hydrochloride, which is an important starting material in preparing pharmaceuticals. Specially it can be used in the process for the preparation of irinotecan.

BACKGROUND OF THE INVENTION

Irinotecan hydrochloride, (S)-4,11-diethyl-3,4,12,14-tetrahydro-4-hydroxy-3,14-dioxo-1H-pyrano[3',4':6,7]-indolizino[1,2-b]quinolin-9-yl [1,4'-bipiperidine]-1'-carboxylate hydrochloride or 7-ethyl-10-[4-(1-piperidino)-1-piperidino]carbonyloxycamptothecin hydrochloride, having the formula I

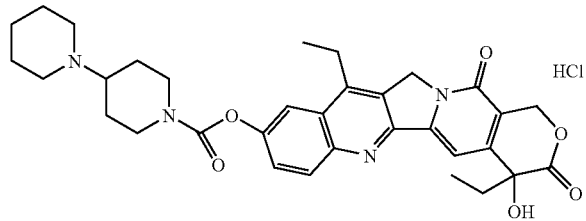

is a camptothecin analog and topoisomerase I inhibitor. Its trihydrate form has been approved in 1996 in the United States for the treatment of colon cancer, but it is also of interest for treatment of other cancers, such as cancers of the lung, the stomach and the pancreas.

Irinotecan is usually prepared semisynthetically from natural camptothecin, which occurs in a Chinese tree, *Camptotheca acuminata*. U.S. Pat. No. 4,604,463 describes several camptothecin derivatives, including irinotecan, its pharmaceutically acceptable salts and preparation thereof starting from natural camptothecin. U.S. Pat. No. 6,121,451 discloses intermediates and process for the synthesis of camptothecin derivatives, e.g. irinotecan hydrochloride.

Sawada et al., Chem. Pharm. Bull. 39(6), 1446-1454 (1991), describes the preparation of irinotecan hydrochloride trihydrate from natural camptothecin in five steps and about 20% of overall yield.

All preparation methods for irinotecan mentioned above include the reaction of 7-ethyl-10-hydroxy camptothecin with [1,4']bipiperidinyl-1'-carbonyl chloride.

The present invention relates to a process for the preparation of [1,4']bipiperidinyl-1'-carbonyl chloride or its hydrochloride, which can be used e.g. as a starting material in the preparation of irinotecan.

Preparation of [1,4']bipiperidinyl-1'-carbonyl chloride has been described in U.S. Pat. No. 4,604,463 so that it can be made by a reaction of an amine with phosgene or diphosgene in a solvent. Suitable solvents mentioned are benzene, toluene or the like aromatic hydrocarbons and hexane or the like aliphatic hydrocarbons. CA reference 2002:975660 (JP 2002371061) describes a process where tetrahydrofurane and hexane are used as solvents. In the process of CA 1997: 389121 (JP 09110865) the solvent is benzene. In Henegar (J. Org. Chem. 62 (1997), 6588-6597) the solvent used in this step is toluene. Using these solvents in the process considerable amounts of dimer and other impurities which are difficult to remove, are formed. The presence of dimer decreases the yield in the preparation of irinotecan and also the quality and color of irinotecan is improved with lower amount of dimer. Different approach to the preparation of [1,4']bipiperidinyl-1'-carbonyl chloride hydrochloride has been described in EP 976733 where the compound is prepared via trialkylsilyl compound using methylene chloride as a solvent.

Now the inventor has surprisingly noticed that if [1,4'] bipiperidinyl-1'-carbonyl chloride or its hydrochloride is made by the reaction of 4-piperidino-piperidene with phosgene using methylene chloride as a solvent, the produced [1,4']bipiperidinyl-1'-carbonyl chloride hydrochloride or base liberated from it contains dramatically reduced amounts of dimer. Other impurities can be removed by using an additional solvent in the distillation of the reaction solvent, which enables the raising of the distillation temperature.

DETAILED DESCRIPTION OF THE INVENTION

The present invention is related to a process for the preparation of [1,4']bipiperidinyl-1'-carbonyl chloride or its hydrochloride, which is a useful intermediate e.g. in the preparation of irinotecan. The use of methylene chloride as a solvent in the reaction of 4-piperidinopiperidine with phosgene and the removal of the reaction solvent by using an additional distillation solvent to raise the distillation temperature gives [1,4'] bipiperidinyl-1'-carbonyl chloride hydrochloride in high yield and purity. The amount of dimer impurity will be less than 5%, even less than 1%.

Another aspect of the present invention is the use of the [1,4']bipiperidinyl-1'-carbonyl chloride or its hydrochloride made according to the invention as a starting material in the preparation of irinotecan, which can also be achieved in high yield and purity.

According to the invention [1,4']bipiperidinyl-1'-carbonyl chloride hydrochloride is made by a reaction of 4-piperidinopiperidine with phosgene using methylene chloride as a solvent. Instead of phosgene also diphosgene or triphosgene can be used. In the reaction with amines diphosgene or triphosgene is first converted to phosgene. The most convenient form to use is triphosgene, which is a solid compound, and it is used in this reaction 1.2 to 2.0 ekv, preferably 1.3-1.5 ekv (as phosgene) of 4-piperidinopiperidine.

After the reaction is completed a suitable aprotic solvent e.g. acetonitrile is added to the reaction mixture, and part of the solvent is distilled off. Other suitable solvents are other nitriles, esters or ketones, where 1,4']bipiperidinyl-1'-carbonyl chloride hydrochloride is soluble but which do not react with it. The addition of the solvent can be made either before distillation or during the distillation, e.g. after about half of the solvent is distilled off. Distillation temperature can be higher when additional solvent is used, and this improves the removal of impurities. The additional solvent is selected so that the distillation can be continued until the temperature rises to 50° C.-70° C. If acetonitrile is used as an additional solvent, the ratio of acetonitrile to methylene chloride at that temperature is between 60:40 and 90:10 vol/vol. In one embodiment of the invention the final distillation temperature is from 60° C. to 65° C., and then the ratio of acetonitrile to methylene chloride is between about 70:30 and 80:20 vol/vol. In this distillation also extra phosgene is removed, and there will be no impurities originating from phosgene in the product.

After the distillation a suitable crystallization solvent is added. Suitable solvents are aromatic and aliphatic hydrocarbons, esters, ketones and ethers. Preferably toluene is used. The crystalline product is isolated by any suitable method known in the art, e.g. filtration or centrifugation may be used. Optionally nitrogen can be used as protecting gas during the reaction and isolation.

Optionally, if a base [1,4']bipiperidinyl-1'-carbonyl chloride is the desired product, the solution after distillation is treated with an aqueous solution of a weak base such as sodium bicarbonate or potassium carbonate. This solution containing the base can be used as such in the preparation of irinotecan.

In the preparation of highly pure irinotecan it is important that the starting materials are also pure. If [1,4']bipiperidinyl-1'-carbonyl chloride or its hydrochloride made by the method of the invention is used in the preparation of irinotecan by reacting it with 7-ethyl-10-hydroxy camptothecin e.g. as described in U.S. Pat. No. 6,121,451, highly pure irinotecan or its hydrochloride may be produced. Crystalline [1,4']bipiperidinyl-1'-carbonyl chloride is unstable, and therefore the preferred reagent is its hydrochloride, which is first liberated to a base.

EXAMPLES

Example 1

[1,4']bipiperidinyl-1'-carbonyl chloride hydrochloride

Scrubber system was used during the reaction and distillation. Phosgene is formed during the reaction.

Triphosgene (100 g) was dissolved in 1280 ml of methylene chloride. Solution of 129.5 g of 4-piperidinopiperidine was dissolved in 1280 ml of methylene chloride and this solution was added at 20-25° C. into the triphosgene solution while cooling the mixture (exothermic reaction). Part of the methylene chloride (1500 ml) was distilled off. Acetonitrile (580 ml) was added gradually. Methylene chloride was distilled off until the temperature rose to 63° C. Toluene (2000 ml) was added gradually. The mixture was cooled to room temperature. The crystalline compound was filtered and washed with toluene (about 1000 ml). The compound was dried under reduced pressure at about 40° C.

The yield was 175.9 g (85.5%)

HPLC purity 99.2%, dimeric impurity 0.8%.

Example 2

[1,4']bipiperidinyl-1'-carbonyl chloride

[1,4']bipiperidinyl-1'-carbonyl chloride hydrochloride (9.7 g), methylene chloride (150 ml) and $K_2CO_3$ (10.5 g, 2.1 ekv) were charged. The mixture was stirred for about 1 hour. The solution was filtered and the cake washed with 10 ml of methylene chloride. The solution (containing 8.4 g of [1,4'] bipiperidinyl-1'-carbonyl chloride) can be used as such for the preparation of Irinotecan Example 3

7-ethyl-10-[4-(1-piperidino)-1-piperidino]carbonyloxy-camptothecin hydrochloride (irinotecan)

7-Ethyl-10-hydroxycamptothecin * $H_2O$ (10 g) and pyridine (120 ml) were charged. A solution of [1,4']bipiperidinyl-1'-carbonyl chloride hydrochloride (9.6 g) and triethylamine (8.5 ml) in methylene chloride (150 ml) was added. The mixture was stirred for 2 hours at room temperature. The mixture was distilled to dryness under reduced pressure. Water (150 ml) was added and the pH was adjusted to 4.0 by hydrochloric acid (5%) at about 80° C. The mixture was cooled to 0-5° C. and stirred for about 20 hours. The crystalline compound was filtered and washed with water. The product was dried under reduced pressure. The yield was 13.2 g (80%).

Example 4

7-ethyl-10-[4-(1-piperidino)-1-piperidino]carbonyloxy-camptothecin hydrochloride (irinotecan)

7-Ethyl-10-hydroxycamptothecin (4.5 g) and pyridine (60 ml) were charged in a reaction vessel. A solution of [1,4']-bipiperidinyl-1'-carbonyl chloride hydrochloride (3.44 g) and triethylamine (4.8 ml) in 75 ml of methylene chloride was added at 30-40° C. The mixture was stirred for 1.5 hours at 30-40° C. 4-piperidinopiperidine (0.58 g) was added and the mixture was stirred for 0.5 hour. Methylene chloride and pyridine were distilled off until the volume of the residue was about 25 ml. Acetonitrile (100 ml) was added and the mixture was heated to about 60° C. The mixture was cooled to room temperature and 15 ml of 5% aqueous hydrochloric acid was added. The mixture was stirred about 20 hours at room temperature. The mixture was cooled to 0±5. The crystalline compound was filtered and washed with acetonitrile:water 10:1 mixture (10 ml) and acetonitrile (10 ml).

The product was dried under reduced pressure. The yield was 6.4 g (90%).

The invention claimed is:

1. A process for the preparation of [1,4']bipiperidinyl-1'-carbonyl chloride hydrochloride comprising:
   a) reacting 4-piperidino-piperidine with phosgene in methylene chloride as a solvent,
   b) adding a suitable aprotic solvent,
   c) distilling off part of the solvent, and
   d) crystallizing [1,4']bipiperidinyl-1'-carbonyl chloride hydrochloride from a suitable solvent.

2. The process of claim 1 wherein the solvent in step d) is toluene.

3. The process of claim 1 further comprising:
   reacting [1,4']bipiperidinyl-1'-carbonyl chloride with 7-ethyl-10-hydroxy camptothecin to produce irinotecan, or its pharmaceutically acceptable salt.

4. The process of claim 1 where the aprotic solvent in step b) is acetonitrile.

5. The process of claim 1 wherein the distilling in step c) is continued until the temperature rises at least to 50° C.

6. The process of claim 1 wherein the distilling in step c) is continued until the temperature rises at least to 60° C.

7. The process of claim 1, wherein the [1,4']bipiperidinyl-1'-carbonyl chloride hydrochloride that is prepared contains less than 5% dimer impurity.

8. The process of claim 1, wherein the [1,4']bipiperidinyl-1'-carbonyl chloride hydrochloride that is prepared contains less than 1% dimer impurity.

9. The process of claim 1, wherein triphosgene is used at 1.2 to 2.0 equivalents as phosgene of 4-piperidinopiperidine.

10. The process of claim 1, wherein triphosgene is used at 1.3 to 1.5 equivalents as phosgene of 4-piperidinopiperidine.

* * * * *